(12) United States Patent
Katta et al.

(10) Patent No.: US 9,237,765 B2
(45) Date of Patent: Jan. 19, 2016

(54) NON-DIGESTIBLE HYDROXYPROPYL STARCH HYDROLYSATE, METHOD FOR PRODUCTION THEREOF AND FOOD AND BEVERAGE

(75) Inventors: Yasuo Katta, Itami (JP); Toyohide Nishibata, Itami (JP); Makoto Tachibe, Itami (JP)

(73) Assignee: MATSUTANI CHEMICAL INDUSTRY CO., LTD., Hyogo (JP)

( * ) Notice: Subject to any disclaimer, the term of this patent is extended or adjusted under 35 U.S.C. 154(b) by 856 days.

(21) Appl. No.: 12/667,514

(22) PCT Filed: Jul. 3, 2008

(86) PCT No.: PCT/JP2008/062078
§ 371 (c)(1),
(2), (4) Date: Dec. 31, 2009

(87) PCT Pub. No.: WO2009/005129
PCT Pub. Date: Jan. 8, 2009

(65) Prior Publication Data
US 2010/0330257 A1    Dec. 30, 2010

(30) Foreign Application Priority Data
Jul. 3, 2007    (JP) .................................. 2007-175002

(51) Int. Cl.
*A23L 1/308*    (2006.01)
*A23G 9/34*    (2006.01)
(Continued)

(52) U.S. Cl.
CPC ................. *A23L 1/3081* (2013.01); *A23G 9/34* (2013.01); *A23L 1/095* (2013.01); *A23L 2/02* (2013.01);
(Continued)

(58) Field of Classification Search
CPC .............................. A23L 1/3081; A23G 9/34
See application file for complete search history.

(56) References Cited

U.S. PATENT DOCUMENTS 3,505,110 A    4/1970  Kesler et al.
4,619,831 A *  10/1986 Sharma .......................... 426/93
(Continued)

FOREIGN PATENT DOCUMENTS

JP    03-247258 A    11/1991
JP    05-504484 A     7/1993
(Continued)

OTHER PUBLICATIONS

Machine Translation of JP 09-294547. Published Nov. 18, 1997 to Hishikawa et al. pp. 1-9.*
(Continued)

*Primary Examiner* — Jenna A Watts
(74) *Attorney, Agent, or Firm* — Sughrue Mion, PLLC

(57) ABSTRACT

The present invention provides a non-digestible hydroxypropyl starch hydrolysate which can be used as novel water soluble dietary fiber, a method for producing it, as well as food products and beverages containing the non-digestible hydroxypropyl starch hydrolysate. The present invention provides the non-digestible hydroxypropyl starch hydrolysate characterized by having a DE value of less than 20 and a glucose content of less than 3% by mass; food products and beverages containing it; and the method for producing the non-digestible hydroxypropyl starch hydrolysate comprising the steps of: (A) hydrolyzing a hydroxypropyl starch with a degree of substitution of 0.05 to 0.4 with α-amylase and then with glucoamylase; and (B) removing glucose from the hydrolysate obtained in the step (A).

1 Claim, 1 Drawing Sheet

(51) Int. Cl.
    *A23L 1/09*         (2006.01)
    *A23L 2/02*         (2006.01)
    *A23L 2/52*         (2006.01)
    *C08B 31/00*       (2006.01)
    *C08B 31/12*       (2006.01)
    *C12P 19/14*       (2006.01)
    *C12P 19/20*       (2006.01)

(52) U.S. Cl.
    CPC ............... *A23L 2/52* (2013.01); *C08B 31/006* (2013.01); *C08B 31/12* (2013.01); *C12P 19/14* (2013.01); *C12P 19/20* (2013.01); *A23V 2002/00* (2013.01)

(56) References Cited

U.S. PATENT DOCUMENTS 5,110,612 A       5/1992     Quarles et al.
5,294,453 A  *  3/1994     Quarles et al. ............... 426/548
5,519,011 A       5/1996     Wakabayashi et al.

FOREIGN PATENT DOCUMENTS

JP       07-014331 B2     7/1993
JP       09-294547 A      11/1997

OTHER PUBLICATIONS

Mitsubishi Chemical "MCI Gel" Technical Information 2008-2009. pp. 1-7.*
"Ion Exchange Technologies". Available online from novasep.com as of Nov. 29, 2006. pp. 1-4.*
B. M. N. Mohd. Azemi, et al., "In Vitro Digestibility of Hydroxypropyl Maize, Waxy Maize and High Amylose Maize Starches", Starch / Stárke, 1984, vol. 36, Nr. 8, S., pp. 273-275.
Japanese Office Action issued in corresponding Japanese Application No. 2007-175002.
Knowledge of starch products, Jun. 25, 2006, pp. 99-100.

* cited by examiner

NON-DIGESTIBLE HYDROXYPROPYL STARCH HYDROLYSATE, METHOD FOR PRODUCTION THEREOF AND FOOD AND BEVERAGE

TECHNICAL FIELD

The present invention relates to non-digestible hydroxypropyl starch hydrolysate, which barely contains a digestible component, a method for producing the same, food products and beverages containing the non-digestible hydroxypropyl starch hydrolysate.

BACKGROUND ART

In the food industry, a hydroxypropyl starch is widely used as a main raw material or auxiliary material of various processed food products. The hydroxypropyl starch is a modified starch obtained by acting propylene oxide on starch. Introduction of a hydroxypropyl group increases hydrophilicity, lowers temperature to initiate gelatinization, and improves performance in water retention, retrogradation stability, or freeze resistance. Therefore, taking advantage of these properties, it has been widely used in foods in general including instant foods such as LL (Long Life) noodles, various chilled and/or frozen foods, and bread.

On the other hand, a hydroxypropyl starch is known to exhibit resistance to an amylase and to be difficult to be digested. Non-patent Document 1 describes digestibility of the hydroxypropyl starch against a pancreatic amylase. It reports that a hydroxypropyl starch derived from corn starch, waxy corn starch, and high amylose corn starch showed, as its molar degree of substitution increases, a decrease in its digestive efficiency to the pancreatic amylase after gelatinization in all samples tested.

As an example using these properties, Patent Document 1 discloses that a method for producing a sugar substitute with low calorie and non-cariosity, which substitute is obtained by hydrolyzing the hydroxypropyl starch to a DE value of 1 to 30. Furthermore, Patent Document 2 discloses a hydrolysate of the hydroxypropyl starch having the DE value of 20 to 45 and containing at least 15% by mass of DP 2 to 6 and the use thereof as a low calorie bulking agent of a sweetener with high sweetness.

Thus, although there are prior arts on the hydrolysate of the hydroxypropyl starch, all are related to hydrolyzation products (mixtures) obtained by simply hydrolyzing the hydroxypropyl starch with an enzyme or acid. These contain many digestible components and cannot necessarily be sufficient as a low calorie dietary fiber material.

[Non-patent Document 1] Mohd et al., *Starch/Staerke*, 36 (7) 273-275 1984

[Patent Document 1] U.S. Pat. No. 3,505,110

[Patent Document 2] Japanese Patent Publication H07-14331 B

DISCLOSURE OF THE INVENTION

Problems Which the Invention Tries to Solve

An object of the present invention is to provide a non-digestible hydroxypropyl starch hydrolysate which can be used as novel water soluble dietary fiber and a method for producing it as well as food products and beverages containing the non-digestible hydroxypropyl starch hydrolysate.

Means for Solving the Problems

The present inventors pay their attention to a digestible component contained in the hydroxypropyl starch, as a result of examining an efficient method for eliminating such a component, have succeeded in obtaining the non-digestible hydroxypropyl starch hydrolysate which can be used as novel water soluble dietary fiber by hydrolyzing the hydroxypropyl starch having a specific degree of substitution using an α-amylase, and then a glucoamylase to convert into glucose and then removing glucose by a procedure, such as chromatographic fractionation or membrane fractionation, to thereby complete the present invention. Hence, the present invention provides, as shown below, the non-digestible hydroxypropyl starch hydrolysate which can be used as the new water soluble dietary fiber, food products and beverages containing the non-digestible hydroxypropyl starch hydrolysate.

1. A non-digestible hydroxypropyl starch hydrolysate having a DE value of less than 20 and a glucose content of less than 5% by mass.
2. The non-digestible hydroxypropyl starch hydrolysate according to the above-mentioned 1 having a dietary fiber content of 80% by mass or more.
3. The non-digestible hydroxypropyl starch hydrolysate according to the above-mentioned 1 or 2, which is further hydrogenated.
4. A food and beverage product comprising the non-digestible hydroxypropyl starch hydrolysate according to any one of the above-mentioned 1 to 3.
5. A method for producing a non-digestible hydroxypropyl starch hydrolysate, the method comprising the steps of: (A) hydrolyzing a hydroxypropyl starch with a degree of substitution of 0.05 to 0.4 with α-amylase and then with glucoamylase; and (B) removing glucose from the hydrolysate obtained in the step (A).
6. The method for producing a non-digestible hydroxypropyl starch hydrolysate according to the above-mentioned 5, wherein the step (B) is fractionation with a polystyrene-based ion-exchange resin or a membrane separation process with a reverse osmosis membrane.

Effects of the Invention

The non-digestible hydroxypropyl starch hydrolysate as the novel water soluble dietary fiber obtained by the present invention is expected to have physical properties such as low sweet taste, low viscosity, non-retrogradation and high moisture retaining property, and various physiological functions as the water soluble dietary fiber. It can be used in many fields including various food products and beverages such as soft drinks, alcoholic beverages such as beer and sparkling wine, ice creams, desserts, bread, confectionaries, and seasonings such as dressings, fishery and/or livestock product pastes, and a low calorie sweetener; pet foods; as well as cosmetics such as a shampoo, rinse, face lotion, and hand cream.

DETAILED DESCRIPTIONS OF THE INVENTION

In the present invention, the term "DE" is an abbreviation for Dextrose Equivalent (glucose equivalent), and is an index widely used for expressing a degree of hydrolysis of a starch hydrolysate. That is, reducing sugars are measured as glucose and the percentage of the reducing sugars to the solid content of 100 is taken as a DE value. Although there were various kinds of methods for measuring this reducing sugar, the Willstatter-Schudel method was used in the present invention.

In the present invention, the term "non-digestible" means a property of not being hydrolyzed by human gastrointestinal tract enzymes. In addition, a "digestible component" means a component which is hydrolyzed by human gastrointestinal tract enzymes.

In the present invention, the term "dietary fiber" is expressed with a value measured by a high-performance liquid chromatography (enzyme-HPLC method) described in Eishin No. 13 (regarding, for example, to a method for analyzing nutritional components and the like in nutrition labeling standards) (pages 415 to 423 of "Hand book for newly developed foods" Chuo Hoki Shuppan Co., Ltd., published on Sep. 25, 1999).

In the present invention, an "average molecular weight" means a number average molecular weight analyzed under the following conditions:

Column: TSKgel™ G2500PWXL, G3000PWXL, G6000PWXL (manufactured by TOSOH CORP.)
Column temperature: 80° C.
Mobile phase: distilled water
Flow rate: 0.5 ml/min
Detector: differential refractive index meter
Sample injection amount: 1% (by mass) solution 100 μl
Calibration curve: pullulan reference standard (eight types between molecular weights 788,000 and 5,900), maltotriose (molecular weight 504) and glucose (molecular weight 180).

The number average molecular weight is calculated by the following formula:

(Number average molecular weight $(Mn)=\Sigma Hi/\Sigma(Hi/Mi)$)

($Hi$: Peak Height, $Mi$: Molecular Weight)

In the present invention, the term "degree of substitution" represents a molar equivalent of the hydroxyl group substituted per glucose unit (per mol). The degree of hydroxypropyl substitution can be measured in accordance with the method of Johnson (*Analytical Chemistry* Vol. 41, No. 6, 859-860, 1969).

Raw material starch used for manufacturing the hydroxypropyl starch used in the present invention is not particularly restricted. Examples thereof include starch of potatoes, tapioca, corn, wheat, rice, and the like, as well as waxy starch of these. Moreover, this hydroxypropyl starch may or may not be slightly cross-linked by phosphoric acids or the like. Although the degree of substitution of the hydroxypropyl starch, it is preferably 0.05 to 0.4. In cases where it is less than 0.05, a yield of the non-digestible component obtained from the hydroxypropyl starch decreases, and its average molecular weight also decreases. Moreover, it is not easy to produce the hydroxypropyl starch having a degree of substitution of more than 0.4. The molecular weight of the non-digestible component obtained from such a hydroxypropyl starch is large and thus its viscosity increases.

Next, the process (A) of the present invention, that is, a method for hydrolyzing a hydroxypropyl starch will be described. For instance, this hydroxypropyl starch is suspended in water to attain about Baume 22 degree. Using chemicals such as calcium carbonate and oxalic acid, pH is adjusted to 5.5 to 6.5, preferably to 6.0. Thereafter, α-amylase is added in an amount of 0.05 to 0.3% by mass based on the solid content. The mixture is hydrolyzed using an appropriate heating apparatus, for example, a heat-pressure cooker, a jet cooker or the like at a heating temperature of 80 to 100° C. for 30 to 60 minutes to liquefy the starch. Thereafter, the enzyme reaction is terminated by a pressure inactivation treatment at 0.2 MPa for 10 minutes or addition of an acid such as oxalic acid. Thereby, hydrolyzation of the hydroxypropyl starch progresses to the limiting point of hydrolyzation with α-amylase. After cooling, pH is adjusted to 4.5, glucoamylase is added in an amount of 0.05 to 0.4% by mass based on the solid content. The mixture was hydrolyzed at 50 to 60° C. preferably 55° C. for about 6 to 24 hours to hydrolyze all digestible components into glucose. And then temperature is increased to about 80° C. to stop the enzyme reaction. By these treatments, a mixture composed of non-digestible hydroxypropyl starch hydrolysate and glucose can be obtained.

Next, preferably after adding activated charcoals into this mixture and decolorization and/or filtration, and purifying by desalting using ion exchange resins, the process (B) of the present invention, that is, removal of glucose, is carried out. The removal of glucose is, for example, in the case of a chromatographic fractionation method, the purified mixture solution is concentrated to obtain a solution with a concentration of about 50% by mass. This solution is flown into a strongly acidic cation-exchange resin column and separated into a polymeric component (non-digestible hydroxypropyl starch hydrolysate) and glucose, and the polymeric component is collected. As the strongly acidic cation-exchange resin used in this case, those which are generally commercially available can be used. Examples thereof include Amberlite™ CG400, CG6000, CR1320 (manufactured by Rohm and Haas Company), Diaion™ UBK-530, 530K (manufactured by Mitsubishi Chemical, Inc.) and Dowex™ PT90322-1 (manufactured by the Dow Chemical Company). Since such resins are for separating glucose from a polymeric component with a larger molecular weight than it, it is preferred to use a Na form or K form.

Moreover, in the case of membrane fractionation, the purified mixture solution is concentrated to obtain a solution with a concentration of about 20 to 30% by mass. Using the membrane separation apparatus equipped with a nanofiltration membrane having a salt blocking rate of about 30 to 70%, circulation concentration is carried out at an operating pressure of 1 to 3 MPa to discharge glucose as a filtrate out of the system. Since the concentration increases by the concentration, it is preferred to carry out a diafiltration mode by which an equal amount of water is added to the filtrate during the operation. As the nanofiltration membrane, those which are generally commercially available can be widely used. Examples thereof include NTR™-7430HG, 7450HG, 7470HG and 7250HG (manufactured by Nitto Denko Corporation). In addition, a method of removing glucose by adding alcohol to precipitate and obtain the non-digestible hydroxypropyl starch hydrolysate and a method of removing glucose by adding yeast for utilization of glucose can be used.

After removing glucose, by a conventional method, decolorization and condensation are carried out, followed by spray drying, to thereby obtain a powdered product. Or it can also be a liquefied product by concentrating to about 70% by masse as a finishing concentration.

The non-digestible hydroxypropyl starch hydrolysate obtained from the hydroxypropyl starch having a degree of substitution of 0.05 to 0.4 in this manner has a DE value of less than 20, preferably less than 18, still more preferably less than 16. The glucose contents is less than 5% by mass, preferably less than 3% by mass, still more preferably less than 1% by mass. The dietary fiber content quantified by the enzyme-HPLC method is 80% by mass or more, preferably 85% by mass or more, still more preferably 90% by mass or more. The average molecular weight is distributed between 600 and 1600. It can be confirmed that the obtained non-digestible hydroxypropyl starch hydrolysate has high moisture retaining property and is highly hydrophilic, compared with a common starch hydrolyzation product.

Furthermore, this non-digestible hydroxypropyl starch hydrolysate can also be subjected to a hydrogenation treatment (reduction) by a conventional method. Since the carbonyl group, which is a reducing end, is changed to an alcohol group by this hydrogenation, colorization caused by a Maillard reaction hardly occurs, and sweetness also is fresh and sharp. In addition, the DE value, glucose content, dietary fiber content and average molecular weight of this non-digestible hydroxypropyl starch hydrolysate (reduced product) subjected to the hydrogenation treatment are almost same as those of the non-digestible hydroxypropyl starch hydrolysate before the hydrogenation treatment.

The non-digestible hydroxypropyl starch hydrolysate and its processed product subjected to the hydrogenation (reduction) according to the present invention are expected to have physical properties such as low sweet taste, low viscosity, non-retrogradation and high moisture retaining property, and various physiological functions as the water soluble dietary fiber. It can be used in many fields including various food products and beverages such as soft drinks, alcoholic beverages such as beer and sparkling wine, ice creams, desserts, bread, confectionaries, and seasonings such as dressings, fishery and/or livestock product pastes, and a low calorie sweetener; pet foods; as well as cosmetics such as a shampoo, rinse, face lotion, and hand cream.

EXAMPLES

The present invention will be described in more detail below in reference to Experiment Example and Examples, but the present invention is not limited thereto.

Experiment Example 1

Sodium sulfate 600 g was dissolved in water 2.8 L as a stabilizing agent. Potato starch 2 kg and 3% (by mass) sodium hydroxide aqueous solution 500 g were added to this to prepare starch slurry. Two parts by mass, 7.5 parts by mass, 15 parts by mass, 22 parts by mass, 30 parts by mass, and 40 parts by mass of propylene oxide were respectively added to 100 parts by mass of starch. The mixture was allowed to react at 30° C. for 24 hours. The resultant was neutralized with sulfuric acid, washed with water, dehydrated and dried, to thereby obtain samples Nos. 1 to 6 of hydroxypropyl starch, respectively. Starch particles in the sample No. 6 were swollen while washed and thus the sample was washed using ethanol. The degree of substitution of these samples is 0.016, 0.058, 0.106, 0.142, 0.190 and 0.420, respectively.

Example 1

Each of the samples Nos. 1 to 6 of hydroxypropyl starch (1 kg) prepared in Experiment Example 1 was suspended in water to make an emulsion (Baumé 22 degree). Calcium carbonate was added to adjust to pH 6.0. And α-amylase (Termamyl™ 120 L, manufactured by Novozymes Japan) (0.1% by mass) was added. The mixture was put into a heat-pressure cooker, while vapor was being introduced, such that a product temperature was 95° C. The mixture was maintained for 30 minutes and then the enzyme was inactivated by increasing the temperature to 130° C., to thereby terminate the liquefaction of starch. The resultant was allowed to cool to 60° C. and adjusted to pH 4.5. Glucoamylase (Gluczyme™ NL4.2, manufactured by Amano Enzyme Inc.) 0.4% by mass was added for hydrolysis at 55° C. for 15 hours, to thereby hydrolyze digestible components to glucose. After the reaction, the enzyme was inactivated by increasing the temperature to 80° C. The resultant was purified by decolorizing filtration with activated charcoal and desalted with ion-exchange resins, and condensed to a concentration of 50% by mass. This aqueous solution was heated to 60° C. and was introduced into a simulated moving bed continuous liquid chromatograph (manufactured by Hitachi Ltd.) equipped with a column filled with DOWEX™ PT90322-1 (Na form, manufactured by Dow Chemical Company) to separate it into a polymeric fraction and glucose by running at an operation temperature of 60° C. The polymeric fraction containing the separated non-digestible hydroxypropyl starch hydrolysate was concentrated and then spray dried, to thereby obtain a powder form of the non-digestible hydroxypropyl starch hydrolysate. With regard to the obtained non-digestible hydroxypropyl starch hydrolysate, a yield from a raw material, hydroxypropyl starch, a dietary fiber content measured by the enzyme-HPLC method, a DE value and glucose content were analyzed. The results are summarized in Table 1. The DE value was measured by the predetermined method. The glucose content was measured as monosaccharide using an HPLC column for sugar content analysis under conditions below.

Column: MCI GEL CK04SS (manufactured by Mitsubishi Chemical Corporation)
Detector: differential refractive index meter
Column temperature: 80° C.
Flow rate: 0.3 ml/minute
Mobile phase: Distilled water
Sample injection amount: 5% by mass, solution 10 μl

TABLE 1

| Hydroxypropyl starch | | Non-digestible hydroxypropyl starch hydrolysate | | | |
|---|---|---|---|---|---|
| Sample No. | Degree of substitution | Yield (% by mass) | Dietary fiber (% by mass) | DE | Glucose* (% by mass) |
| No. 1 | 0.016 | 4.9 | 89.2 | 25.3 | 2.2 / 93.7 |
| No. 2 | 0.058 | 20.2 | 91.8 | 18.9 | 1.0 / 74.2 |
| No. 3 | 0.106 | 32.0 | 92.5 | 15.3 | 1.1 / 59.1 |
| No. 4 | 0.142 | 41.0 | 92.5 | 13.0 | 0.8 / 47.7 |
| No. 5 | 0.190 | 43.4 | 92.3 | 12.8 | 1.2 / 44.6 |
| No. 6 | 0.420 | 43.9 | 93.1 | 12.0 | 0.5 / 43.9 |

*A value in the lower row is a value before fractionation.

From the results in Table 1, it is seen that, depending on the degree of substitution of the hydroxypropyl starch, the yield and dietary fiber content of the obtained non-digestible hydroxypropyl starch hydrolysate increase, and, particularly, in cases where the degree of substitution is at least 0.05, good results can be obtained.

Example 2

Sodium sulfate 2 kg was dissolved in 13 L of water. Potato starch 10 kg and 3% (by mass) sodium hydroxide aqueous solution 2.7 kg were added to this to prepare starch slurry. Propylene oxide (10 parts by mass) was added to starch 100 parts by mass. The mixture was allowed to react at 40° C. for 20 hours to prepare a hydroxypropyl starch (degree of substitution 0.153). This hydroxypropyl starch 5 kg was suspended in water to make an emulsion (Baumé 20 degree). Calcium carbonate was added to adjust to pH 6.0. And α-amylase (Termamyl™ 120 L, manufactured by Novozymes Japan) (0.1% by mass) was added. The mixture was put into a pressure reaction vessel, while vapor was being introduced, such that a product temperature was 95° C. The mixture was maintained for 30 minutes and then the enzyme was inactivated by increasing the temperature to 130° C. and by keeping the temperature for 30 minutes, thereby ending the liquefaction of starch. The resultant was allowed to cool to 60° C. and adjusted to pH 4.5. Glucoamylase (Gluczyme™ NL4.2, manufactured y Amano Enzyme Inc.) 0.4% by mass was added for hydrolysis at 55° C. for 15 hours, thereby hydrolyzing digestible components to glucose. After the reaction, the enzyme was inactivated by increasing the temperature to 80° C. The resultant was purified by decolorizing filtration with activated charcoal and desalted with ion-exchange resins, and condensed to a concentration of 50% by mass. This aqueous solution was heated to 60° C. and was introduced into a simulated moving bed continuous liquid chromatograph (manufactured by Hitachi Ltd.) equipped with a column filled with Amberlite™ CR1320 Na (manufactured by Rohm and Haas Company) to separate it into a macro polymeric fraction and glucose by running at an operation temperature of 60° C. The polymeric fraction containing the separated non-digestible hydroxypropyl starch hydrolysate was concentrated and then spray dried, to thereby obtain 2 kg of a powder form of the non-digestible hydroxypropyl starch hydrolysate. The obtained non-digestible hydroxypropyl starch hydrolysate had a dietary fiber content of 88.8%, a DE value of 14.6, by mass, a glucose content of 0.3% by mass (the content before fractionation 39.4% by mass) and an average molecular weight of 810.

Example 3

A commercially available hydroxypropylated phosphoric acid cross-linked starch (degree of substitution: 0.091, product name: Farinex™ VA70TJ, manufactured by Matsutani Chemical Industry Co., Ltd.) (15 kg) was hydrolyzed in the same manner as described in Example 2, to thereby obtain a mixture of non-digestible hydroxypropyl starch hydrolysate and glucose. This solution was adjusted to 20% by mass. And 60 L of the resulting solution was subjected to an operation (diafiltration) in which a cycle operation was carried out using a membrane separation apparatus Membrane Masters RUW-5A™ (Nitto Denko Corporation) equipped with NTR™-7450HG (having a salt blocking rate of 50%) as a nanofilteration membrane under conditions of an operation temperature 60° C., an operation pressure of 1.5 MPa, and a circulation flow rate of 8 L/min to concentrate to 30 L (two-fold condensation/concentration) followed by addition of 30 L of water. The operation was repeated six times. Glucose was removed as a filtrate to obtain 30 L of a concentrated solution of non-digestible hydroxypropyl starch hydrolysate (concentration 14% by mass). Activated charcoal was added to this solution for decolorization and filtered, and then the resultant was concentrated to a concentration of 70% by mass, to thereby obtain 5.5 kg of a liquefied product of the non-digestible hydroxypropyl starch hydrolysate. The obtained non-digestible hydroxypropyl starch hydrolysate had a DE value of 15.8, a dietary fiber content of 90.5% by mass, a glucose content of 0.8% by mass.

Example 4

The non-digestible hydroxypropyl starch hydrolysate (DE value 13.0) 1 kg derived from the sample No. 4 prepared in Example 1 was diluted with water to a concentration of 65% by mass. The resulting solution was placed in a 2 L autoclave (manufactured by NAC-Autoclave). And 20 g of Raney nickel (R239, manufactured by Nikko Rica Co.) was added and pH was adjusted to 9.6 using 7.2% (by mass) disodium hydrogen phosphate aqueous solution and 21% (by mass) sodium hydroxide aqueous solution. Thereafter, hydrogen gas was introduced at 100 kg/cm$^2$ and a hydrogenation reaction was carried out at 130° C. for 2 hours. After the reaction, Raney nickel was removed and the resulting product was purified with activated charcoal and ion-exchange resins. And then the resultant was concentrated to a concentration of 70% by mass, to thereby obtain 560 g of a reduced product of the non-digestible hydroxypropyl starch hydrolysate.

Example 5

Water activity and moisture absorption and release of the non-digestible hydroxypropyl starch hydrolysate (DE value 14.6) prepared in Example 2 was measured in comparison with Glystar™ (DE value 15, glucose content 1.1% by mass, dietary fiber content 0.0% by mass, manufactured by Matsutani Chemical Industry Co., Ltd.), which is a commercially available starch hydrolyzation product.

<Measurement of Water Activity>

A 65, 70, and 75% by mass aqueous solution of each sample was prepared and its water activity was measured at 25° C. using a water activity meter TH-2 (manufactured by Novasina). The results are shown in FIG. 1.

<Measurement of Moisture Absorption and Release>

A 70% by mass aqueous solution of each sample was prepared and placed at 20° C. in a constant humidity desiccator adjusted with a saturated solution of reagents shown in Table 2. The weight was measured with time to prepare a moisture absorption and release curve. The results are shown in FIG. 2.

TABLE 2

| Relative humidity at 20° C. (%) | Saturated aqueous solution in the desiccator |
|---|---|
| RH100 (100) | Distilled water |
| RH75 (75) | NaCl |
| RH52 (52) | NaHSO$_4$•H$_2$O |

From the result of a comparative study with a starch hydrolyzation product with almost same DE value, the non-digestible hydroxypropyl starch hydrolysate had a higher effect of decreasing the water activity and higher moisture absorption and lower moisture release and thus its affinity to water was presumably very high. A novel property which has not been present in a conventional starch hydrolyzation product was discovered.

Example 6

Using the non-digestible hydroxypropyl starch hydrolysate (DE value 12.8) originated from the sample No. 5, which was prepared in Example 1, powdered materials were mixed and dissolved in water in accordance with the formulation shown in Table 3. Thereafter, fruit juice, puree, perfumes and the like were added and homogenized by a homomixer to prepare mango juice. By the addition of the non-digestible hydroxypropyl starch hydrolysate, not only was dietary fiber provided but also fruity and juicy taste were improved, compared with the control product.

TABLE 3

|  | Control | Sample |
| --- | --- | --- |
| Transparent mango juice (concentrated) | 5.0 | 5.0 |
| Mango puree | 5.0 | 5.0 |
| Fructose glucose liquid sugar | 5.0 | 5.0 |
| Granulated sugar | 3.0 | 3.0 |
| Citric acid | 0.03 | 0.03 |
| Sodium citrate | 0.01 | 0.01 |
| Flavor | 0.1 | 0.1 |
| Non-digestible hydroxypropyl starch hydrolysate | — | 3.0 |
| Water | to 100 g | to 100 g |
| The amount of dietary fiber* (g/100 g) | — | 2.8 |

*A calculated value from the added amount

Example 7

Using the non-digestible hydroxypropyl starch hydrolysate (DE value 13.0) originated from the sample No. 4, which was prepared in Example 1, all raw materials except for a flavor were mixed in accordance with the formulation shown in Table 4. The mixture was heated to 85° C., stirred using a homomixer and further homogenized with a homogenizer, followed by aging in a refrigerator (5° C.) for 12 hours. Subsequently, the flavor was added. After freezing, the mixture was rapidly frozen to −30° C. to prepare ice cream. By the addition of the non-digestible hydroxypropyl starch hydrolysate, not only was dietary fiber provided but also milk feelings were improved, compared with a control product.

TABLE 4

|  | Control | Sample |
| --- | --- | --- |
| Fresh cream | 19.5 | 19.5 |
| Powdered skim milk | 8.0 | 8.0 |
| Sugar | 12.0 | 12.0 |
| Egg yellow | 2.0 | 2.0 |
| Stabilizing agent | 0.2 | 0.2 |
| Vanilla flavor | 0.1 | 0.1 |
| Starch syrup (in terms of solid content, DE40) | 5.0 | — |
| Non-digestible hydroxypropyl starch hydrolysate | — | 5.0 |
| Water | to 100 g | to 100 g |
| The amount of dietary fiber* (g/100 g) | — | 4.6 |

*A calculated value from the added amount

Example 8

Using the non-digestible hydroxypropyl starch hydrolysate prepared in Example 3, unsweetened bean paste and granulated sugar were placed in a pan in accordance with the formulation shown in Table 5, heated and boiled down. Before the end of boiling down, salt and the non-digestible hydroxypropyl starch hydrolysate were added and boiled down to a degree of sugar of 60 to attain a weight of about 170 g. The mixture was allowed to cool, to thereby prepare azuki bean paste. By the addition of the non-digestible hydroxypropyl starch hydrolysate, not only was dietary fiber provided but also a moisture retaining property was improved, compared with a control product.

TABLE 5

|  | Control | Sample |
| --- | --- | --- |
| Unsweetened azuki bean paste | 100 | 100 |
| Granulated sugar | 70 | 50 |
| Salt | 0.15 | 0.15 |
| Non-digestible hydroxypropyl starch hydrolysate (in terms of the solid content) | — | 20 |
| Water | 50 | 50 |
| The amount of dietary fiber* (g/100 g) | — | 11.8 |

*A calculated value from the added amount

Figure 1:
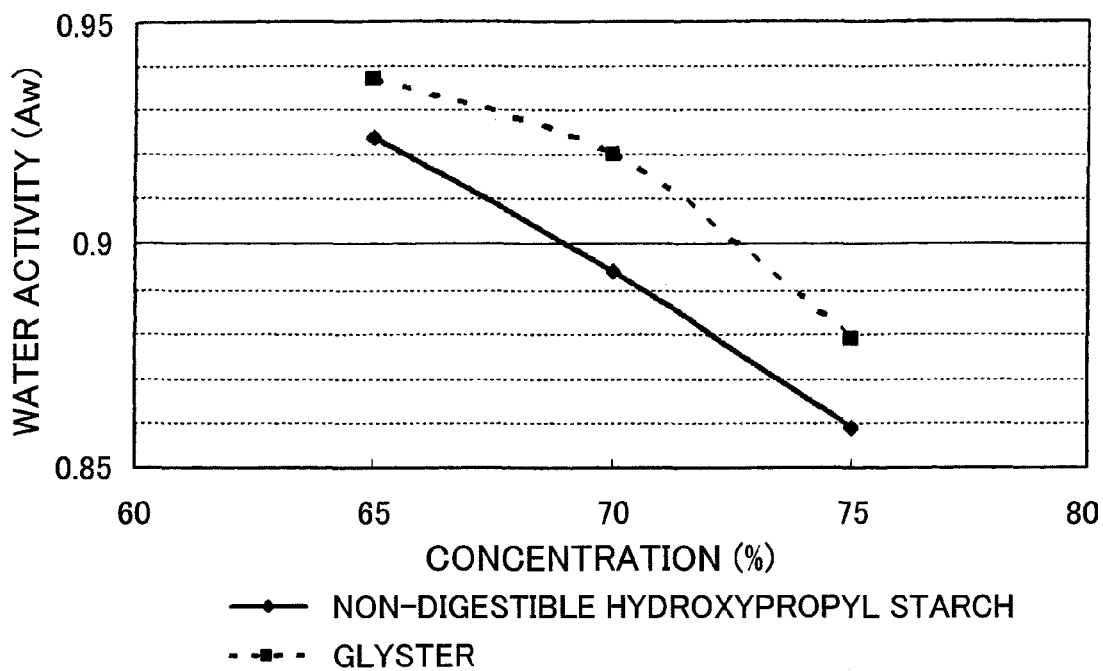
FIG. 1 shows a figure comparing the water activity of the non-digestible hydroxypropyl starch hydrolysate with that of a commercially available starch hydrolyzation product (Glystar™).
Figure 2:
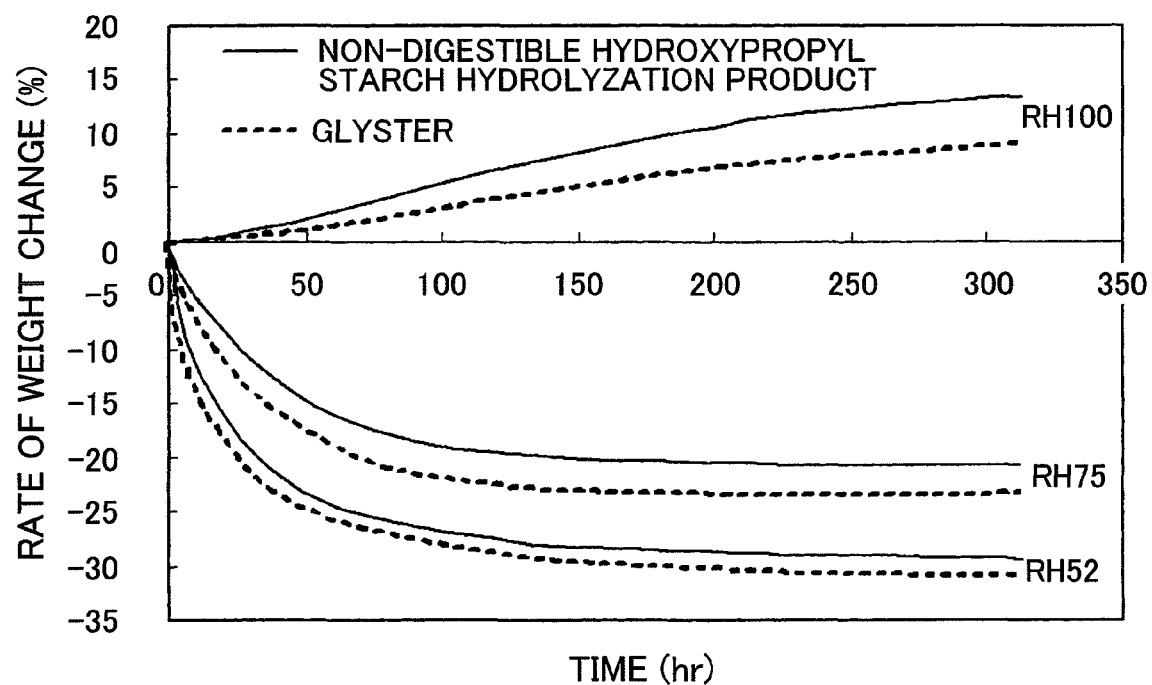
FIG. 2 shows a figure comparing moisture absorption and release of the non-digestible hydroxypropyl starch hydrolysate with that of a commercially available starch hydrolyzation product (Glystar™).

What is claimed is:

1. A method for producing a non-digestible hydroxypropyl starch hydrolysate, said method comprising the steps of:
    (A) hydrolyzing a hydroxypropyl starch with a degree of substitution of 0.05 to 0.4 with α-amylase and then with glucoamylase to give a mixture of a non-digestible hydroxypropyl starch hydrolysate and glucose; and
    (B) removing the glucose from the mixture obtained in the step (A) to obtain a non-digestible hydroxypropyl starch hydrolysate having a DE value of less than 20, a dietary fiber content of 90% by mass or more and a glucose content of less than 3% by mass,
    wherein the step (B) is a fractionation with a polystyrene-based ion-exchange resin or a membrane separation process with a reverse osmosis membrane.

* * * * *